United States Patent [19]
Izhar et al.

[11] Patent Number: 5,444,179
[45] Date of Patent: Aug. 22, 1995

[54] INFRA SHORT-DAY STRAWBERRY TYPES

[75] Inventors: Shamay Izhar; Eva Izsak, both of Rehovot, Israel, 76251

[73] Assignee: State of Israel, Ministry of Agriculture, Bet Dagan, Israel

[21] Appl. No.: 876,838

[22] Filed: Apr. 30, 1992

Related U.S. Application Data

[63] Continuation of Ser. No. 735,969, Jul. 25, 1991, Pat. No. Plant 7,881, and a continuation of Ser. No. 735,968, Jul. 25, 1991, Pat. No. Plant 7,869, and a continuation of Ser. No. 735,970, Jul. 25, 1991, Pat. No. Plant 7,870, and a continuation of Ser. No. 735,967, Jul. 25, 1991, Pat. No. Plant 7,865, and a continuation of Ser. No. 735,695, Jul. 25, 1991, Pat. No. Plant 7,876, and a continuation of Ser. No. 823,638, Jan. 22, 1992, Pat. No. Plant 8,746, and a continuation of Ser. No. 823,802, Jan. 22, 1992, Pat. No. Plant 8,748, and a continuation of Ser. No. 823,721, Jan. 22, 1992, Pat. No. Plant 8,747, said Ser. No. 735,969, is a continuation of Ser. No. 490,103, Mar. 6, 1990, abandoned, said Ser. No. 735,968, is a continuation of Ser. No. 489,440, Mar. 6, 1990, abandoned, said Ser. No. 735,970, is a continuation of Ser. No. 491,758, Mar. 6, 1990, abandoned, said Ser. No. 735,967, is a continuation of Ser. No. 490,102, Mar. 6, 1990, abandoned, said Ser. No. 735,695, is a continuation of Ser. No. 489,407, Mar. 6, 1990, abandoned.

[30] Foreign Application Priority Data

| Mar. 17, 1989 | [IL] | Israel | 1430/89 |
| Mar. 17, 1989 | [IL] | Israel | 1431/89 |
| Mar. 17, 1989 | [IL] | Israel | 1432/89 |
| Mar. 8, 1991 | [IL] | Israel | 1671/91 |
| Apr. 10, 1991 | [IL] | Israel | 1679/91 |
| Apr. 10, 1991 | [IL] | Israel | 1680/91 |

[51] Int. Cl.$^6$ .......... A01H 1/04; A01H 5/00; A01H 5/08

[52] U.S. Cl. .......... 800/200; 800/DIG. 64; 800/DIG. 37; 47/58

[58] Field of Search .......... PLT/48, 49; 47/58; 800/200, DIG. 64, DIG. 37

[56] References Cited

U.S. PATENT DOCUMENTS

| P.P. 3,561 | 1/1974 | Bringhurst et al. | Plt./48 |
| P.P. 4,487 | 11/1979 | Bringhurst et al. | Plt./49 |
| P.P. 5,262 | 7/1984 | Voth et al. | Plt./48 |
| P.P. 5,263 | 7/1984 | Voth et al. | Plt./48 |
| P.P. 5,264 | 7/1984 | Bringhurst et al. | Plt./48 |
| P.P. 5,267 | 8/1984 | Bringhurst et al. | Plt./49 |
| P.P. 5,268 | 8/1984 | Voth et al. | Plt./48 |
| P.P. 6,578 | 1/1989 | Voth et al. | Plt./48 |
| P.P. 7,024 | 9/1989 | Johnson et al. | Plt./49 |
| P.P. 7,172 | 2/1990 | Voth et al. | Plt./49 |
| P.P. 7,865 | 5/1992 | Izsak et al. | Plt./48 |
| P.P. 7,869 | 5/1992 | Izsak et al. | Plt./48 |
| P.P. 7,870 | 5/1992 | Izsak et al. | Plt./48 |
| P.P. 7,876 | 6/1992 | Izsak et al. | Plt./48 |
| P.P. 7,881 | 6/1992 | Izsak et al. | Plt./48 |

OTHER PUBLICATIONS

Dubinsky, V., The Influence of daylength and night temperature on early flowering in strawberry. M. Sc. Thesis, The Hebrew University of Jerusalem; Rehovot, Israel (Hebrew original and English translation) 1985.

Darrow, G. M., 1966, in The Strawberry: History, Breeding and Physiology, Ch. 19, pp. 314–354, Holt, Rinehart and Winston; New York, Chicago, San Francisco.

Guttridge, C. G., 1985, Fragaria x Ananassa, in CRC Handbook of Flowering, vol. III, Halevy, A., ed.

Wareing, P. F. and Phillips, I. D. J., 1978, in The Control of Growth and Differentiation in Plants, p. 202, Pergamon Press.

(List continued on next page.)

Primary Examiner—David T. Fox
Assistant Examiner—Erich E. Veitenheimer
Attorney, Agent, or Firm—Pennie & Edmonds

[57] ABSTRACT

The present invention relates to an infra short-day strawberry type and methods for selection as well as induction of flowering of the infra short-day type by subjecting the plant to a relatively long light regime under short-day conditions accompanied by night temperatures from about 10° C. to about 26° C.

7 Claims, No Drawings

OTHER PUBLICATIONS

Izsak, E. and Izhar, S., 1983, The importance of day length and night temperature on earliness in strawberry. Hassadeh 63:2100–2103 (Hebrew original and English translation).

Izsak, E. and Izhar, S., 1984, Breeding and testing of early strawberry varieties in the central and the northern Negev regions. Hassadeh 64:1774–1777 (Hebrew original and English translation).

Izsak, E. and Izhar, S., 1984, "Rachel": a new early variety of strawberry for export. Hassadeh 64:1778–1781 (Hebrew original and English translation).

Heide. 1977. Physiol. Plant. 40:21–26.

Stushnoff et al. 1983. In Methods in Fruit Breeding. Moore et al. editors. Chapter 16:267–273.

Downs, R. J. and Piringer, A. A., 1955, Differences in Photoperiodic responses of everbearing and June-bearing strawberries, Proc. Amer. Soc. Hort. Sci. 66:234–236.

Howard, C. M. and Albregts, E. E., 1980, "Dover" strawberry. HortScience 15(4):540.

Bringhurst, R. S. and Voth, V., 1989, California Strawberry Cultivars. Fruit Var. J. 43(1):12–19.

Izsak, E. and Izhar, S., Registration No. 370/82, registered Nov. 26, 1984 under State of Israel Plant Breeders' Rights Law of 1973 for strawberry variety 'Rachel'.

Izsak, E., 1978, "Nurit": new early variety for export. Hassadeh 59:443–446 (Hebrew original and English translation).

INFRA SHORT-DAY STRAWBERRY TYPES

This application is a continuation of the following applications:
1. U.S. Plant patent application Ser. No. 07/735,969, filed Jul. 25, 1991, now U.S. Plant Pat. No. PP07881, issued Jun. 9, 1992, which is a continuation of U.S. Plant patent application Ser. No. 07/490,103, filed Mar. 6, 1990, now abandoned.
2. U.S. Plant patent application Ser. No. 07/735,968, filed Jul. 25, 1991, now U.S. Plant Pat. No. PP07869, issued May 19, 1992, which is a continuation of U.S. Plant patent application Ser. No. 07/489,440, filed Mar. 6, 1990, now abandoned.
3. U.S. Plant patent application Ser. No. 07/735,970, filed Jul. 25, 1991, now U.S. Plant Pat. No. PP07870, issued May 19, 1992, which is a continuation of U.S. Plant patent application Ser. No. 07/491,758, filed Mar. 6, 1990, now abandoned, which in turn claims priority of Israel application No. 1432/89, filed Mar. 17, 1989.
4. U.S. Plant patent application Ser. No. 07/735,967, filed Jul. 25, 1991, now U.S. Plant Pat. No. PP07865, issued May 12, 1992, which is a continuation of U.S. Plant patent application Ser. No. 07/490,102, filed Mar. 6, 1990, now abandoned, which in turn claims priority of Israel application No. 1431/89, filed Mar. 17, 1989.
5. U.S. Plant patent application Ser. No. 07/735,695, filed Jul. 25, 1991, now U.S. Plant Pat. No. PP07876, issued June 2, 1992, which is a continuation of U.S. Plant patent application Ser. No. 07/489,407, filed Mar. 6, 1990, now abandoned, which in turn claims priority of Israel application No. 1430/89, filed Mar. 17, 1989.
6. U.S. Plant patent application Ser. No. 07/823,638, filed Jan. 22, 1992, now U.S. Plant Pat. No. PP8746, which in turn claims priority of Israel application No. 1671/91, filed Mar. 8, 1991.
7. U.S. Plant patent application Ser. No. 07/823,802, filed Jan. 22, 1992, now U.S. Plant Pat. No. PP8748, which in turn claims priority of Israel application No. 1680/91, filed Apr. 10, 1991.
8. U.S. Plant patent application Ser. No. 07/823,721, filed Jan. 22, 1992, now U.S. Plant Pat. No. PP8747, which in turn claims priority of Israel application No. 1679/91, filed Apr. 10, 1991.

INTRODUCTION

The present invention relates to early flowering strawberry types and methods for selection of such types as well as induction of flowering in early flowering strawberry types such that flower bud primordia are initiated in response to relatively long light regimes under short-day conditions while being subjected to night temperatures ranging from about 10° C. to about 26° C. The identification and commercialization of a strawberry type having such properties will result in fall, early winter and summer fruit production.

BACKGROUND OF THE INVENTION

The genetic control of flowering in higher plants in general, and strawberry in particular, has remained unsolved despite recent advances in the fields of plant breeding and molecular biology. It is well known that the induction of flowering in higher plants involves the interaction of genetic factors and environmental cues. The family Rosaceae, of which *Fragaria ananassa* (cultivated strawberry) is a member, is an excellent example. Cultivated strawberry, an octaploid resulting from a cross between *F. chiloensis* and *F. virginiana*, grows as a rossette. The stem is often referred to as a crown, where growing parts are transformed from vegetative to reproductive growth buds. The reproductive buds develop a cluster of inflorescences carried on a common peduncle.

The environmental conditions promoting either vegetative or reproductive development in strawberry are usually antagonistic (Darrow, 1966, The Strawberry: History, Breeding and Physiology, Ch.19, pp.314–334; Holt, Rinehart and Winston; New York, Chicago, San Francisco; Guttridge, C. G., Fragaria x Ananassa, In: CRC Handbook of Flowering, Vol. III, (Halevi A., ed.), CRC Press (1985), pp. 16–33. Two environmental factors controlling the induction of flowering in strawberry are light (photoperiodism) and temperature (thermoperiodism). Cultivated lines of strawberry have been classified as either short-day (Wareing and Phillips, 1978, The Control of Growth and Differentiation in Plants, p. 202, Pergamon Press), day-neutral (Downs and Pringer, 1955, Proc. Amer. Soc. Hort. Sci. 66:234–236), facultative short-day (Guttridge, 1969, Fragaria The Induction of Flowering. Ch. X, ed. Evans, L. T., Canberra: MacMillan, pp. 247–267) or long-day (Guttridge, supra). The above terminology describes the day length in which induction of floral bud initiation occurs and, hence, a switch from a vegetative to a reproductive phase of development. Therefore, in general terms, a short-day plant requires one to numerous light:dark cycles in which day length is becoming increasingly shorter (e.g., from Jun. 21 to Dec. 21). Conversely, a long-day plant requires one to numerous light:dark cycles in which the day length is becoming increasingly longer (e.g., from Dec. 21–Jun. 21). Therefore, a short-day plant may initiate flower bud primordia when the day length is still relatively long, yet becoming shorter day by day. A day-neutral plant is not markedly affected by the light regime. The classification of some strawberry lines as facultative short-day refers to the fact that these lines may flower even under continuous light provided that the average temperature is about 10° C. (Guttridge, 1969, Fragaria In: The Induction of Flowering. Ch. X, ed. Evans, L. T., Canberra: MacMillan).

The transition from the vegetative to the reproductive phase in Fragaria is of immense economic importance. The commercial strawberry supply is limited from November to February despite the wide geographical dispersion of commercial strawberry plantings. Therefore, it would be advantageous to identify strawberry types that initiate floral bud differentiation earlier than those presently available to the commercial grower.

SUMMARY OF THE INVENTION

The present invention relates to an early flowering strawberry type, herein referred to as "infra short-day" (ISD) type, and methods for selecting such types and inducing flowering in the ISD type such that flower bud primordia are initiated in response to relatively long light regimes under short-day conditions while being subjected to night temperatures ranging from about 10° C. to about 26° C. Strawberry types classified as short-day or day-neutral do not initiate flower bud primordia under the selection and induction regimes of the present invention.

In a particular embodiment of the invention, ISD types may be selected or induced to flower under climatic field conditions represented by about 7-14 light-:dark cycles wherein day length decreases from about 13 hours, 40 minutes to about 13 hours, 20 minutes, with night temperatures of about 22° C.

In a specific embodiment of the invention, the ISD type is selected or induced to flower in central Israel under the climatic field conditions described above. In another specific embodiment of the invention, the ISD type is selected or induced to flower in Southern California under the climatic field conditions described above. In another specific embodiment of the invention, the ISD type is selected or induced to flower in the South of Spain under the climatic conditions described above.

In a further embodiment of the invention, the ISD type is selected or induced to flower under controlled conditions that mimic the climatic regime described above.

The resulting ISD type is then placed into a classical breeding program. Selection of additional ISD types requires screening progeny of specific crosses for plants possessing the ISD response.

The result of the present invention is a strawberry type flowering earlier than classical short-day varieties, and, hence, resulting in earlier fruit production and harvest. The ISD trait of the present invention can be combined with other traits to produce fruit characterized by good taste (with the majority of ISD types possessing high total yield, high soluble solids, as discussed infra), good shape and size as well as a long shelf life. The present invention is not limited to any particular variety of strawberry, but to any strawberry which possesses the ISD characteristic.

DETAILED DESCRIPTION OF THE INVENTION

ENVIRONMENTAL CONDITIONS INDUCING FLOWERING IN AN ISD TYPE

The infra short-day plant is induced to form floral buds under nursery conditions at a day length of approximately 13.5 hours during the summer nursery period of late June–September, which is an unusually long day length for the common Fragaria.

Additionally, the ISD type will differentiate floral buds at night temperatures from about 10° C. to about 26° C. Therefore, the ISD strawberry type may be induced to initiate floral buds under relatively long light regimes under short-day conditions (e.g., about 13.5 hours in the Summer months) and anywhere within a wide range of night temperatures (e.g., from about 10° C. to about 26° C.). The ISD plant will normally flower 6-8 weeks subsequent to floral bud initiation and will begin to yield fruit approximately at weeks 10-12.

The ISD type can also initiate flower induction under classical short-day conditions, but a short-day plant will not be induced to flower under the conditions described above. An ISD variety is further distinguished from other known varieties in that it does not have a chilling requirement. Once the ISD type is induced to flower, it continues to flower and yield fruit (according to the specific variety) until at least the end of the following summer or until the plant undergoes senescence.

The ISD response is defined in general terms as a strawberry variety or line that produces viable fruit in early November. Therefore, it follows that an ISD response in strawberry would require the initiation of flower primordia in mid-August and flowering in late September or early October. This developmental pattern reveals that ISD type plants respond earlier than classical short-day plants in promoting a change from a vegetative to reproductive phase. In other words, initiation of flower bud primordia is stimulated by longer day length than classical short-day strawberry plants (although still technically a "short-day" plant) and higher night temperatures which accompany the longer day length of the summer months in regions such as Central Israel, Southern California and the South of Spain.

Therefore, prior to the present invention, a day length of less than about 10 hours (under short-day conditions) and a night temperature of above about 15° C. were thought to be required to induce flower bud primordia. Longer day length under short-day conditions and high night temperatures (e.g., above about 26°) were considered inhibitory to the induction of floral bud primordia in strawberry.

SELECTION AND BREEDING OF AN INFRA SHORT DAY TYPE

PRE-INDUCTION EXPOSURE TO LONG-DAY CONDITIONS

Briefly, according to the invention, plants are exposed to a long-day light treatment prior to flower induction. In a one embodiment of the invention, the treatment may comprise from 16 to 14 hours of light and 8 to 10 hours of dark, with several breaks of light administered during this dark period. In a specific embodiment of the invention, long-day treatments involve 14 hours of light and 10 hours of dark. This long-day regime may be as important as the induction period itself. One of ordinary skill in the art would be familiar with related procedures to mimic a long-day period.

INITIAL SELECTION OF AN ISD VARIETY

The initial selection procedure involves screening specific genetic crosses between strawberry varieties under either (1) controlled environmental conditions or (2) field nursery conditions described above and selecting progeny exhibiting the ISD response. Either of the two distinct tests available to confirm the ISD response should employ 2-year old plants from seed during their second cycle under nursery conditions.

Strawberry varieties were chosen for a genetic cross with the Israeli variety, "Nurit", on the basis of whether flowers differentiate either under short or relatively long days (e.g., North European sources) or short-days with relatively high night temperatures (e.g., California varieties). A specific genetic cross was conducted with "Nurit" and a European variety, "Pantagruella". Neither parent alone exhibits the ISD type response. Progeny from this cross which exhibited the ISD response were utilized to develop lines for further examination. Line 101, subsequently referred to as "Rachel", is one such line derived from the specific cross between "Nurit" and "Pantagruella" which exhibited the ISD response.

Additional ISD types are selected by utilizing an ISD type as one of the parents in a subsequent genetic cross. Progeny from such a cross which exhibits the ISD type response are utilized to develop lines as described above for "Rachel".

METHODS OF INDUCING FLOWERING IN AN ISD TYPE

As mentioned, above, two distinct tests available to confirm whether a strawberry is an ISD type. Either test should employ 2-year old plants during their second cycle under nursery conditions.

INDUCTION OF FLOWERING OF AN ISD TYPE UNDER NATURAL ENVIRONMENTAL CONDITIONS

The test for an ISD type under natural conditions may be administered in the field nursery. Strawberry plants from the second year removed from true seedlings (e.g., the second season) are planted usually in the nursery in April. Runners with plantlets are produced during the summer. These young plantlets are collected from the nursery and transferred to the production field during the last week of August or the first three weeks of September (according to the specific variety) and planted at that time. An ISD variety will begin to flower profusely 4-6 weeks subsequent to planting.

INDUCTION OF FLOWERING OF AN ISD TYPE UNDER CONTROLLED ENVIRONMENTAL CONDITIONS

A controlled environment, such as a walk-in growth chamber, may be utilized to duplicate the conditions required to distinguish an ISD type from a short-day, long-day or day-neutral type. Therefore, one is not restricted to a particular geographic region in order to practice the present invention. The plants are placed within the controlled environment and subjected to a day length of approximately 13.5-14 hours and a night temperature of about 26° C. Approximately ten cycles (24 hours each) induce floral bud initiation in a typical ISD variety and early flowering and fruit production subsequent to planting under field conditions. Plants responding positively to the light and temperature regime in the growth chamber (e.g., flower initiation) are considered ISD types. As mentioned above, a typical short-day or day neutral plant will not differentiate flowers under these controlled conditions.

EXAMPLE

COMPARISON BETWEEN THE EFFECT OF DAY LENGTH AND NIGHT TEMPERATURE ON FLOWERING IN THE INFRA SHORT-DAY TYPE, "RACHEL", AND THE SHORT DAY TYPE, "TUFTS"

Applicants teach an induction procedure carried out under either natural or controlled environmental conditions to select an ISD type. The short-day strawberry variety has historically been utilized in growing regions such as Israel and California, resulting in a harvest in the late winter and spring months. Therefore, Applicants exemplify their invention by presenting data in Table 1 and Table 2 which clearly indicate that the ISD type of the present invention responds differently to environmental cues than does the classical short-day strawberry type. This differing response shows that ISD type flowers substantially earlier than the classical short-day type. Applicants compare a short-day type from California referred to as "Tufts"(U.S. Plant Pat. No. 3,561) (also known in Israel as "Aliso") to an ISD type of the present invention, "Rachel". The ISD type "Rachel" was selected as described above. Both types were treated prior to floral bud initiation by 14 hours of light and breaking of the dark period with short periods of light. The treatment is well known in the art as a method of imitating the long-day effect. Replicate plants of both types were placed in a three separate growth chambers and subjected to a 14 hour light:10 hour dark cycle for 14 days prior to planting on September 15. The three growth chambers were set to night temperatures of 10° C., 17° C. and 26° C., respectively. The temperature during the light cycle was 26° C. for all treatments. The effect of differing night temperatures is described in Table 1.

TABLE 1

| The effect of night temperature on flowering of "Rachel" and "Tufts" | | | | | | | | |
|---|---|---|---|---|---|---|---|---|
| Type/NT (°C.) | % plants flowering (date) | | | | | | | |
| | 10/1 | 10/15 | 10/30 | 11/15 | 11/30 | 12/15 | 12/30 | 1/15 |
| Rachel | | | | | | | | |
| 10° | 0 | 20 | 50 | 57 | 60 | 100 | 100 | 100 |
| 17° | 0 | 40 | 63 | 82 | 83 | 100 | 100 | 100 |
| 26° | 0 | 20 | 52 | 72 | 82 | 100 | 100 | 100 |
| Tufts | | | | | | | | |
| 10° | 0 | 0 | 0 | 0 | 0 | 0 | 100 | 100 |
| 17° | 0 | 0 | 0 | 0 | 0 | 0 | 100 | 100 |
| 26° | 0 | 0 | 0 | 0 | 0 | 100 | 100 | 100 |

The infra short-day variety, "Rachel", is indifferent to the variation in temperature, whereas the short-day variety, "Tufts", does not flower under the long light regime, regardless of the temperature. "Tufts" eventually flowers, most likely due to the natural light regime subsequent to the September 15 planting in the production field.

Table 2 compares the effect of day length and night temperature on both "Rachel" and "Tufts".

TABLE 2

| Comparison of the effect of day length and night temperatures on "Rachel" and "Tufts" | | | | | | | |
|---|---|---|---|---|---|---|---|
| Type/Treatment | % plants flowering (date) | | | | | | |
| | 10/1 | 10/15 | 10/30 | 11/15 | 11/30 | 12/15 | 12/30 |
| Rachel | | | | | | | |
| SD/17° C. | 0 | 60 | 83 | 85 | 90 | 100 | 100 | 100 |
| SD/26° C. | 0 | 46 | 60 | 65 | 80 | 98 | 98 | 98 |
| LD/17° C. | 0 | 30 | 50 | 52 | 62 | 95 | 95 | 95 |

TABLE 2-continued

Comparison of the effect of day length and night temperatures on "Rachel" and "Tufts"

| Type/Treatment | % plants flowering (date) | | | | | | |
|---|---|---|---|---|---|---|---|
| | 10/1 | 10/15 | 10/30 | 11/15 | 11/30 | 12/15 | 12/30 |
| Tufts | | | | | | | |
| SD/17° C. | 0 | 15 | 15 | 15 | 15 | 62 | 90 | 100 |
| SD/26° C. | 0 | 0 | 0 | 0 | 0 | 60 | 98 | 98 |
| LD/17° C. | 0 | 0 | 0 | 0 | 0 | 20 | 40 | 98 |

SD = short day
LD = long-day

Short light regime cycles consisted of 9 hours light:15 hours dark and long light regime cycles consisted of 15 hours light:9 hours dark. The temperature was 26° C. during all light cycles. Early flowering was recorded for "Rachel" in either short or long light regimes with a 17° C. dark period temperature and under short light regime conditions with a dark period temperature of 26° C. Conversely, "Tufts" flowered only under the more classical short-day condition of a short light regime cycle coupled with a dark temperature of 17° C. As with the data presented in Table 1, "Tufts" eventually flowers, most likely due to response to the natural light regime following transfer from the growth chamber to field conditions.

COMPARATIVE YIELD OF AN INFRA SHORT-DAY STRAWBERRY TYPE TO A SHORT-DAY STRAWBERRY TYPE

Early induction of floral bud initiation leading to early flowering in an infra short-day variety translates into earlier fruit set and harvest of the commercial strawberry. Table 3 indicates that fruit from an ISD type ripens earlier than several classical short-day varieties (e.g., "Douglas" and "Chandler").

TABLE 3

Comparative yield of infra short day types versus short-day types[1]

| | Nov. | Dec. | Jan. | Feb. | Mar. | Apr. |
|---|---|---|---|---|---|---|
| Shalom[2] | 50 | 70 | 80 | 100 | 100 | 70 |
| Sharon[3] | 40 | 60 | 80 | 80 | 80 | 80 |
| Dorit[4] | 30 | 70 | 100 | 100 | 100 | 100 |
| Smadar[5] | 50 | 70 | 100 | 100 | 100 | 50 |
| Saaid[6] | 0 | 70 | 100 | 100 | 100 | 100 |
| Douglas[7] | 0 | 0 | 40 | 150 | 150 | 150 |
| Chandler[8] | 0 | 0 | 30 | 150 | 150 | 120 |

[1]Average yield in g/m² in Ramat Hadar, Israel.
[2]U.S. Plant Pat. No. 7,876 filed July 25, 1991. The time of ripening for "Shalom" fruit is early.
[3]U.S. Plant Pat. No. 7,881 filed July 25, 1991. The time of ripening for "Sharon" fruit is very early.
[4]U.S. Plant Pat. No. 7,869 filed July 25, 1991. The time of ripening for "Dorit" fruit is early.
[5]U.S. Plant Pat. No. 7,865 filed July 25, 1991. The time of ripening for "Smadar" fruit is very early to early.
[6]U.S. Plant Pat. No. 7,870 filed July 25, 1991. The time of ripening for "Saaid" fruit is early to medium.
[7]U.S. Plant Pat. 4,487, which is incorporated herein by reference. The time of ripening for "Douglas" fruit is late.
[8]U.S. Plant Pat. No. 5,262, which is incorporated herein by reference. The time of ripening for "Chandler" fruit is late.

Eight such ISD types are "Shalom" (U.S. Plant Pat. No. 7,876), "Smadar" (U.S. Pat. No. 7,865), "Dorit" (U.S. Plant Pat. No. 7,869), "Sharon" (U.S. Plant Pat. No. 7,881), "Saaid" (U.S. Plant Pat. No. 7,870), "Nama" (U.S. Plant patent application Ser. No. 07/823,721, now U.S. Plant Pat. No. 8747), "Virginia" (U.S. Plant patent application Ser. No. 07/823,802, now U.S. Pat. No. 8748), and "Ofra" (U.S. Plant patent application Ser. No. 07/823,638, now U.S. Plant Pat. No. 8796). These eight U.S. plant patent applications are incorporated herein by reference in their entireties. Mother plants from these strawberry types are stored at 0° C. from January to April. They are then planted in a nursery having long-day light conditions and average temperatures of 30° C. during the day and 22° C. at night without further treatment. Runners with plantlets are produced during the summer. Young plantlets from these ISD types are collected from the nursery in September and transferred to raised beds. Water and fertilizers are applied through drip irrigation. As shown in Table 3 for five of the infra short-day varieties, these varieties yield appreciable levels of fruit in November (except "Saaid") and December. In contrast, neither classical short-day variety tested ("Douglas" and "Chandler") bears fruit until January.

EXAMPLE

COMPARISON OF SHELF-LIFE AND FLAVOR BETWEEN INFRA SHORT-DAY AND SHORT-DAY STRAWBERRY TYPES

Table 4 discloses characteristics of shelf-life and flavor for several ISD types and the short-day type, "Douglas". Total Soluble Solids (T.S.S.), indicative of fruit sweetness, is measured at the time of harvest and is determined with a refractometer. The use of a refractometer to measure T.S.S. of strawberry fruit at the time of harvest is known to one of ordinary skill in the art. Table 4 discloses that representative ISD strawberry varieties are comparable to a typical short-day strawberry type in firmness, sepal appearance, fruit color and marketable appearance, as well as possessing high sugar content as measured by T.S.S. (e.g., the fruit of ISD varieties is characterized by good taste, good shape and size as well as long shelf-life). While T.S.S. may desirably range from about 4 to about 12, the exemplified ISD varieties fall within a range from about 8 to about 9.6. ISD varieties perform very well as described during Fall and mid-winter, while no short-day varieties are capable of bearing fruit at these times. Winter conditions are more difficult than Spring (June-bearing) conditions.

Seeds of the strawberry cultivars "Rachel" and "Nurit" have been deposited with the American Type Tissue Culture Collection, Rockville, Maryland, and have been assigned accession numbers ATCC 75861 and ATCC 75862, respectively.

The present invention is not to be limited in scope by the particular varieties set forth in the specification, since these varieties are intended as examples of the infra short-day strawberry types of the invention. Any plants within the scope of the claims and/or functionally equivalent to the claimed subject matter are within the scope of this invention. Indeed, various modifications of the invention in addition to those shown and described herein will become apparent to those skilled in the art from the forgoing description. Such modifications are intended to fall within the scope of the claims.

TABLE 4

COMPARATIVE SHELF-LIFE AND FLAVOR OF ISD AND SHORT-DAY TYPES

| Variety | Percentage Health | Firmness$^a$ Pressure defects | Visual | Newton units | Sepal appearance$^b$ | Fruit color$^c$ | Marketable appearance$^d$ | Sugar content T.S.S.$^e$ |
|---|---|---|---|---|---|---|---|---|
| *First test: at harvest date* | | | | | | | | |
| Virginia$^f$ | 100 | 0 | 5 | 4.2 | 5 | 3.5 | 4.0 | 8.5 |
| Ofra$^g$ | 100 | 0 | 5 | 6.0 | 5 | 4.0 | 4.5 | 9.6 |
| Nama$^h$ | 100 | 0 | 5 | 3.7 | 5 | 3.5 | 4.0 | 8.0 |
| Douglas$^i$ | 100 | 0 | 5 | 3.7 | 5 | 4.5 | 4.0 | 6.5 |
| *Second test: After 3 days of storage at 2° C.* | | | | | | | | |
| Virginia | 80 | 20 | 3.5 | 3.5 | 4 | 4.2 | 3.8 | |
| Ofra | 92 | 8 | 4.0 | 6.0 | 4 | 4.2 | 4.4 | |
| Nama | 78 | 22 | 3.5 | 3.0 | 4 | 4.0 | 3.7 | |
| Douglas | 76 | 24 | 3.7 | 3.5 | 4 | 5.0 | 3.7 | |
| *Third test: after 3 days storage at 2° C. plus 2 additional days at simulated shelf temperature of 18° C.* | | | | | | | | |
| Virginia | 50 | 50 | 3.0 | 2.8 | 3.0 | 4.5 | 3.2 | |
| Ofra | 55 | 45 | 3.5 | 5.5 | 3.2 | 4.5 | 3.5 | |
| Nama | 44 | 56 | 3.0 | 3.0 | 3.0 | 4.5 | 3.0 | |
| Douglas | 45 | 55 | 3.0 | 3.0 | 3.2 | 5.0 | 3.2 | |

INDEX:
$^a$5-hard 1-soft
$^b$5-green, fresh like, 1-dry, brown
$^c$5-dark red, 1-green, pink
$^d$5-prime 1-not marketable
$^e$Total Soluble Solids (T.S.S.) expresses fruit sweetness and was determined with a refractometer
$^f$U.S. Plant Pat. application Ser. No. 07/823,802, filed January 22, 1992.
$^g$U.S. Plant Pat. application Ser. No. 07/823,638, filed January 22, 1992.
$^h$U.S. Plant Pat. application Ser. No. 07/823,721, filed January 22, 1992.
$^i$U.S. Plant Pat. No. 4,487.

What is claimed is:

1. An isolated strawberry plant which initiates floral buds with no chilling requirement in response to approximately ten cycles of 24 hours each with a day length of approximately 13.5 to 14 hours accompanied by night temperatures of about 26° C. with flowering and fruiting proceeding within about six to eight weeks subsequent to the initiation of floral buds, wherein said isolated strawberry plant is derived from at least one parent tracing its origin to the strawberry cultivar Rachel, ATCC accession number 75861, or the strawberry cultivar Nurit, ATCC accession number 75862.

2. A method for selecting a strawberry plant of claim 1 comprising subjecting a collection of strawberry plants not previously exposed to chilling to approximately ten cycles of 24 hours each with a day length of approximately 13.5 to 14 hours accompanied by night temperatures of about 26° C. and selecting those plants in which flowering and fruiting proceeds within about six to about eight weeks subsequent to the initiating of floral buds.

3. A method of inducing a strawberry plant of claim 1 to initiate floral buds comprising subjecting the plant to a relatively long light regime under short-day conditions accompanied by night temperatures from about 10° C. to about 26° C. with flowering and fruiting proceeding within about six to about eight weeks subsequent to the initiation of floral buds.

4. The method of claim 2 or 3, wherein the light regime has an average day length of about 13.5 to 14 hours.

5. The strawberry plant of claim 1, wherein the light regime has an average day length of about 13.5 to 14 hours.

6. The strawberry plant of claim 5, wherein the total soluble solids of fruit removed from the strawberry plant at the time of harvest as determined with a refractometer is from about 4 to about 12.

7. The strawberry plant of claim 5, wherein the total soluble solids of fruit removed from the strawberry plant at the time of harvest as determined with a refractometer is from about 8 to about 9.6.

* * * * *